United States Patent [19]

Weber et al.

[11] Patent Number: 5,759,172
[45] Date of Patent: Jun. 2, 1998

[54] BALLOON CATHETER WITH LOBED BALLOON AND METHOD FOR MANUFACTURING SUCH A CATHETER

[75] Inventors: Jan Weber, Roden; Johannes Gerardus Maria Van Muiden, Peize, both of Netherlands

[73] Assignee: Cordis Corporation, Miami, Fla.

[21] Appl. No.: 629,720

[22] Filed: Apr. 9, 1996

[51] Int. Cl.$^6$ .................................................. A61M 29/00
[52] U.S. Cl. .............................. 604/96; 604/202; 606/194
[58] Field of Search ............................ 604/96, 205, 202; 606/192, 191, 194

[56] References Cited

U.S. PATENT DOCUMENTS

| | | | |
|---|---|---|---|
| 5,108,370 | 4/1992 | Walinsky | 604/96 |
| 5,318,587 | 6/1994 | Davey | 604/96 X |
| 5,456,666 | 10/1995 | Campbell et al. | 604/96 |
| 5,458,572 | 10/1995 | Campbell et al. | 604/96 |
| 5,470,314 | 11/1995 | Walinsky | 604/96 |
| 5,478,319 | 12/1995 | Campbell et al. | 604/96 |
| 5,484,411 | 1/1996 | Inderbitzen et al. | 604/96 |

FOREIGN PATENT DOCUMENTS

| | | | |
|---|---|---|---|
| WO 93/19802 | 10/1993 | WIPO | A61M 29/00 |
| WO 94/05365 | 3/1994 | WIPO | A61M 29/02 |
| WO 94/23787 | 10/1994 | WIPO | A61M 29/00 |

*Primary Examiner*—Mark Bockelman
*Assistant Examiner*—N. Kent Gring
*Attorney, Agent, or Firm*—Paul A. Coletti

[57] ABSTRACT

The invention relates to a catheter comprising a tube-like basic body with a proximal and a distal end and an expandable balloon member arranged close to the distal end to the basic body. The balloon member comprises a number of relatively stiff sections extending on a small diameter in a longitudinal direction of the basic body and relatively pliable sections extending inbetween, wherein the relatively pliable sections form lobes in an expanded state of the balloon member. The invention furthermore relates to a method for manufacturing a catheter according to the invention, wherein a piece of tube-like basic material is provided and, by blow molding, a balloon member is made in a mold, which is arranged to the bias material. The balloon member is manufactured in the mold cavity of a mold, the cross-section of which is lobated, by receiving a tube-like partial manufacture inside it and deforming it by blow molding into a shape corresponding to that of the shape of the mold cavity.

7 Claims, 3 Drawing Sheets

BALLOON CATHETER WITH LOBED BALLOON AND METHOD FOR MANUFACTURING SUCH A CATHETER

FIELD OF THE INVENTION

The invention relates to a catheter comprising, in the usual manner, a basic tube-like body with a proximal and a distal end and an expandable balloon member arranged close to the distal end of the basic body.

Such balloon catheters, known e.g. from WO 95/17223, are for instance used for the purpose of dilating narrowed blood vessels. During treatment the balloon is advanced via a blood vessel of the patient to the constriction, where it is expanded by supplying a liquid or gas under pressure from the proximal end to the balloon, as a result of which the blood vessel will be dilated at that site.

With this treatment it is often necessary that the balloon is kept in its expanded state for a certain period of time. In the known catheter grooves are formed in the balloon to prevent complete occlusion of the blood vessel during this time, as a result of which the tissue cells upstream from the expanded balloon would be deprived of nourishment and oxygen. If the dilatation treatment would take up too much time the tissue in questions could be damaged.

SUMMARY OF THE INVENTION

The invention relates to a catheter comprising a tube-like basic body with a proximal and a distal end and an expandable balloon member arranged close to the distal end to the basic body. The balloon member comprises a number of relatively stiff sections extending on a small diameter in a longitudinal direction of the basic body and relatively pliable sections extending inbetween, wherein the relatively pliable sections form lobes in an expanded state of the balloon member. The invention furthermore relates to a method for manufacturing a catheter according to the invention, wherein a piece of tube-like basic material is provided and, by blow molding, a balloon member is made in a mold, which is arranged to the bias material. The balloon member is manufactured in the mold cavity of a mold, the cross-section of which is lobed, by receiving a tube-like partial manufacture inside it and deforming it by blow molding into a shape corresponding to that of the shape of the mold cavity. With the catheter according to the invention, its performance is further improved. In the expanded state the lobes carry out the dilatation, while between the lobes channels are formed through which a sufficient amount of blood can flow. The risk that the tissue upstream receives too little nourishment and/or oxygen is consequently removed.

An additional advantage of the stiff bands between the lobes is that they will display an axial bursting direction when the interventionalist applies too much pressure is applied to the material of which the balloon has been made. The axial debris will not damage the blood vessel on removal of the burst balloon.

The relatively stiff parts of the balloon member could be formed by manufacturing them so as to have a greater thickness, or by making them, for example of a fiber-reinforced or cross-linked thermoplastic material respectively. The total, unexpanded diameter of the balloon can consequently remail small.

A very suitable embodiment is characterized when the balloon is of the pre-formed type, the lobes will be able to fold properly, on deflation of the balloon, against the basic body.

The invention also relates to and provides a method for manufacturing a catheter as described above. The basic material (which does not expand in the mold cavity as it is positioned against the inwardly protruding ridges of the lobated mold cavity) retains a relatively greater thickness so that it remains relatively stiff. The intermediate sections which have expanded into the lobes, will obtain a thinner wall and will consequently become relatively pliable.

Preferably using the method as set out herein the relatively stiff parts can consequently obtain a suitable stiffness.

By employing the methods of the invention set out herein, a balloon member can be manufactured of which the relatively stiff sections and the lobes extend in a helical pattern as a result of which this balloon becomes properly foldable.

DESCRIPTION OF THE DRAWINGS

The invention is explained in greater detail in the following description with reference to the attached drawings.

DETAILED DESCRIPTION OF THE INVENTION

Figure 1:
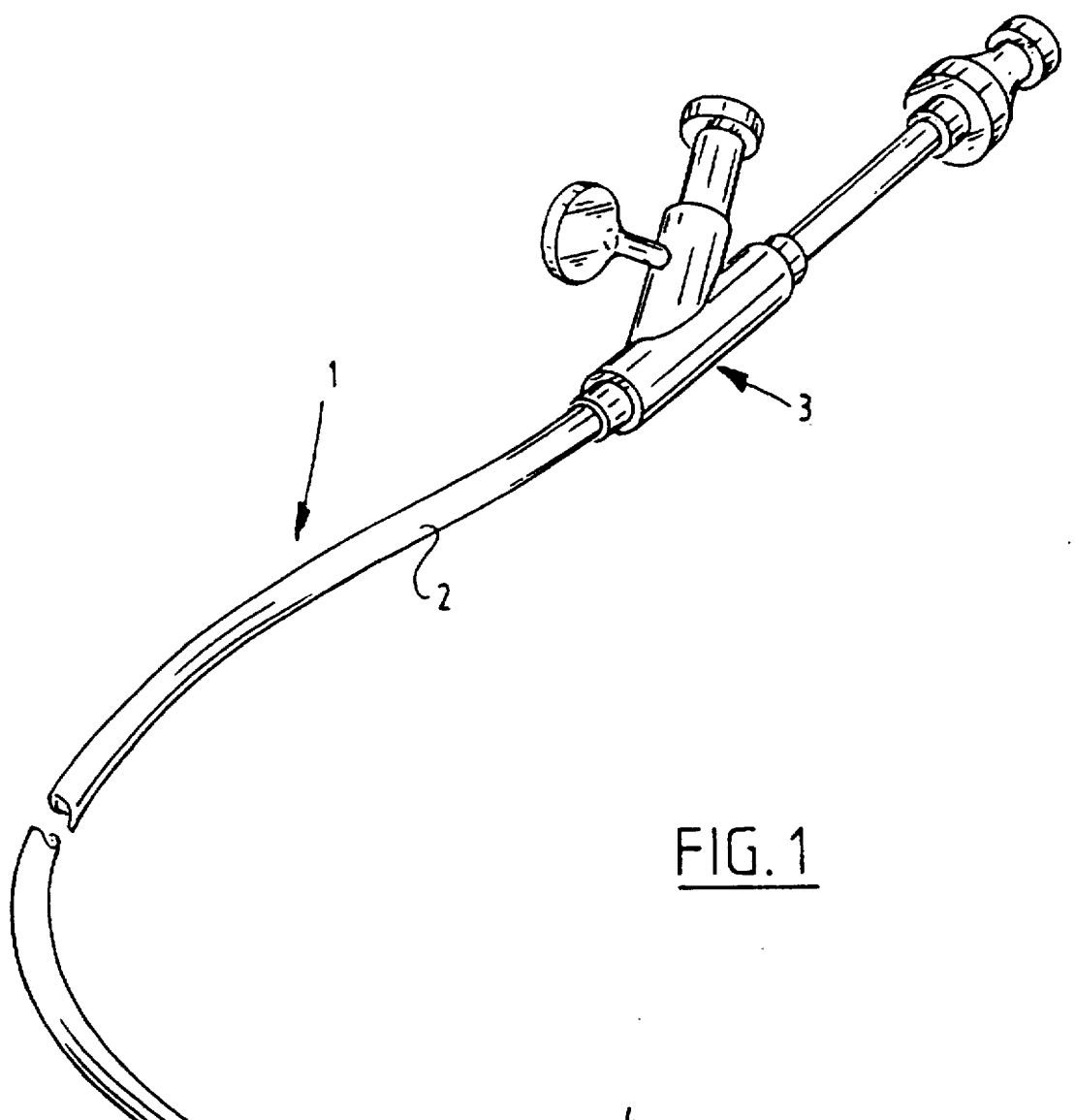
FIG. 1 is a simplified view of a balloon catheter according to the invention during treatment.

The catheter 1 according to the invention shown in FIG. 1 comprises a tube-like basic body with a proximal end 3 and a distal end 4. The distal end 4 is provided with a balloon member 5.

The balloon member 5 has in the illustrated expanded state a number of lobes 8 with channels 9 formed inbetween. In the illustrated position of use, the balloon member 5 of the catheter 1 has been positioned at a constriction formed by deposits 7 inside a blood vessel 6 of a patient. By expanding the balloon member 5, the constriction is treated in a manner known as such. As during the expansion of the balloon member 5 channels 9 are formed inbetween the lobes 8, flow through the blood vessel 6 will not be blocked completely. As has been indicated with the arrows, blood can still flow through the blood vessel 6, also in the expanded state of the balloon 5, so that tissue located upstream from it is not starved of oxygen and nourishment during treatment.

Figure 2:
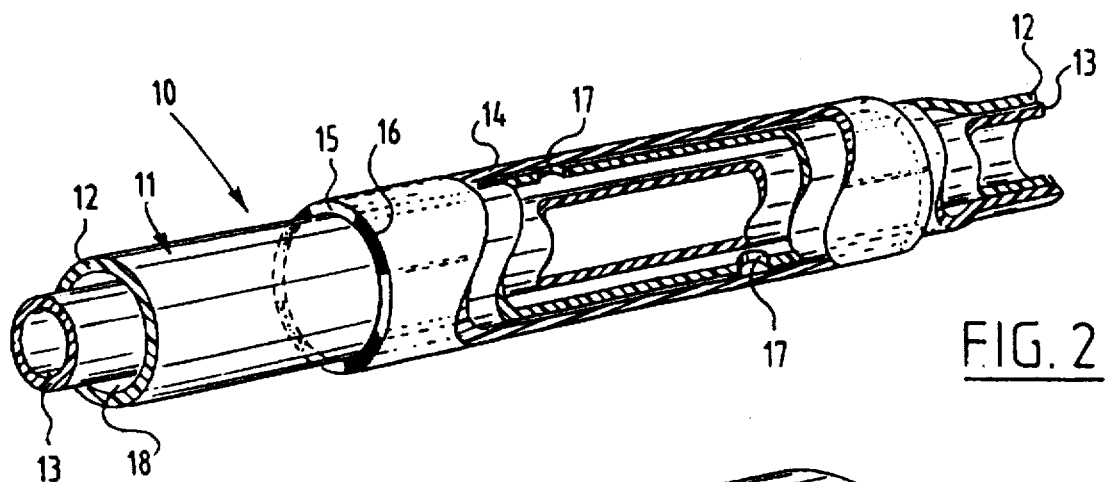
FIG. 2 is a partly broken away perspective view of a distal end-section of a catheter according to a first embodiment of the invention, in which case the balloon member is unexpanded.
Figure 3:
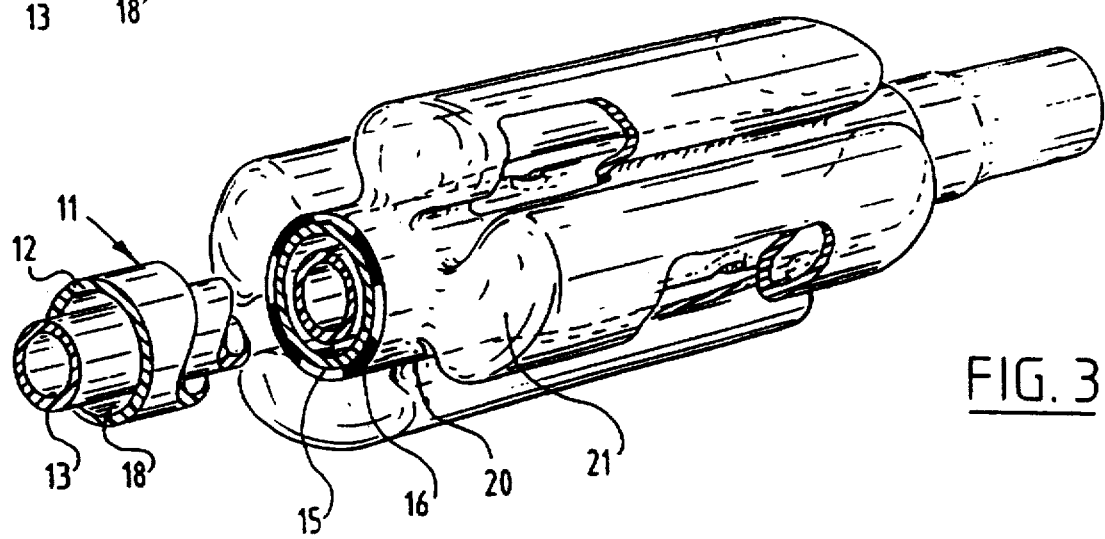
FIG. 3 illustrates the balloon member of FIG. 2 in expanded state.

FIGS. 2 and 3 show in greater detail the distal end of an embodiment of the catheter according to the invention: FIG. 2 in unexpanded state and FIG. 3 in expanded state.

The catheter 10 in these figures comprises a basic body 11 which has been assembled from an outer tube-like body and an inner tube-like body 13 received in a lumen 18 thereof. At the distal end the inner tube-like body 13 is connected with the outer tube-like body 12 around its entire circumference. A balloon member 14 has been arranged to the outer tube-like body 12. With both ends it has been connected with the circumference of the tube-like body 12.

As has been indicated in the FIGS. 2 and 3, the balloon member 14 comprises a number of relatively stiff sections 16 extending substantially in the longitudinal direction of the basic body 11 and relatively pliable sections 15 extending inbetween.

For the purpose of expanding the balloon 14, liquid or gas under pressure is supplied via the lumen 18 from the proximal end. This medium under pressure flows via the openings 17 in the wall of the outer tube-like body 12 into the balloon member 14. As a result of the supplied pressure, the relatively pliable sections 15 of the balloon member 14 expand into lobes 21 as shown in FIG. 3. Channels 20 remain inbetween the lobes 21, as the relatively stiff sections 16 do not expand or expand less.

The relatively stiff sections 16 can be formed because the material of the balloon member 14 has different properties to that of the sections 15. The relatively stiff sections 16 can also be formed by connecting them in a longitudinal direction with the outer tube-like element 12 of the basic body 11, whereas the intermediate, relatively pliable sections 15 will not be connected with the basic body and can consequently expand freely.

Figure 4:
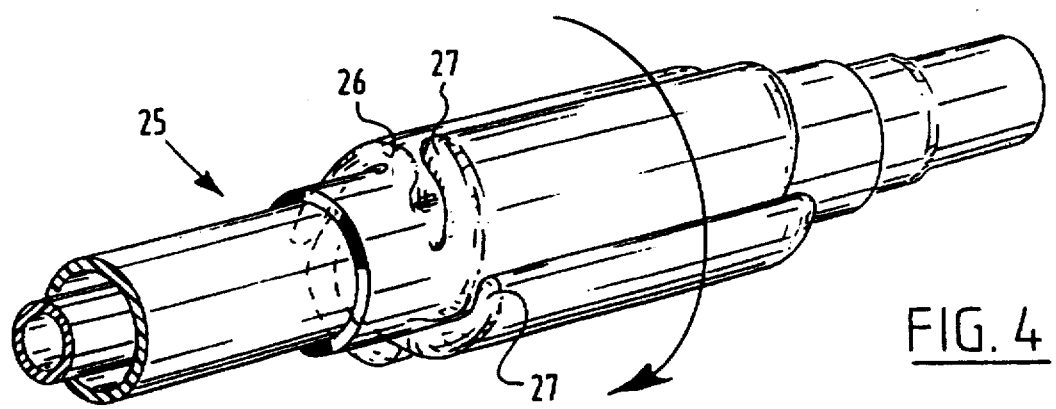
FIG. 4 shows a balloon member of the pre-formed type in unexpanded state.

The balloon member 14 can be manufactured of an elastic material, so that the relatively pliable sections 15 stretch on expansion into the lobes 21 shown in FIG. 3. It is also possible to pre-form the balloon, as a result of which it will obtain the expanded form but can be folded into a smaller diameter. Such an embodiment has been illustrated in FIG. 4. The catheter 25 has a balloon member 26 with pre-formed lobes 27. By rotating the balloon member 26 in the direction indicated by the arrow, the unexpanded lobes are folded against the basic body, so that at the distal end the catheter will obtain a relatively small cross-section. In this state the balloon member can be introduced into a patient.

Figure 5:
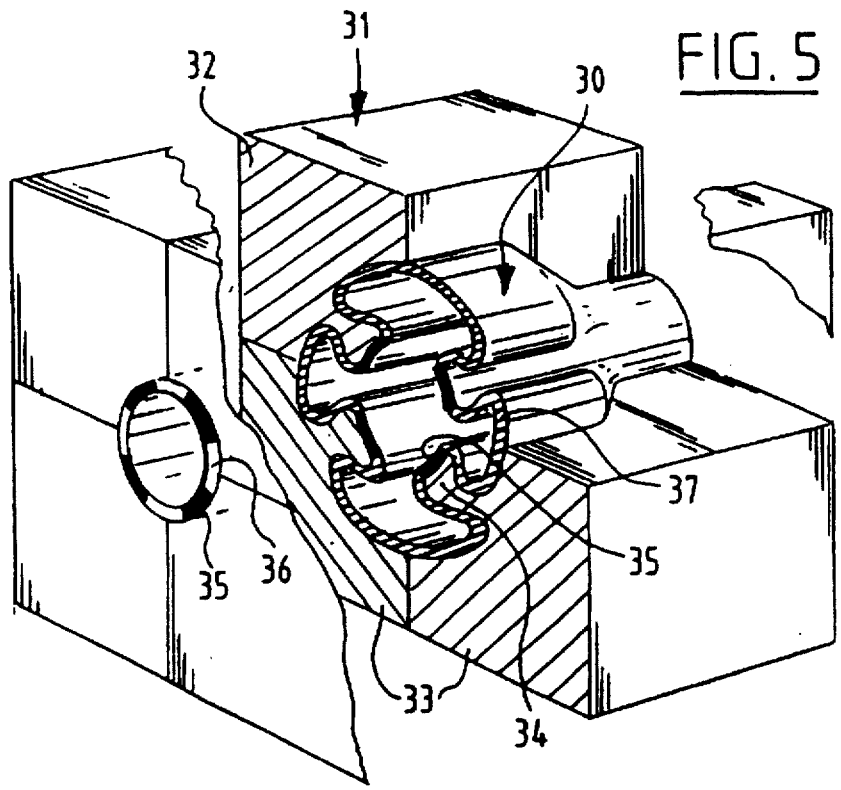
FIG. 5 illustrates schematically the method according to the invention.

FIG. 5 illustrates schematically a method for manufacturing a balloon member for a catheter according to the invention. With the method shown here, a balloon member 30 of the pre-formed type is manufactured. For this purpose a mold 31 is used which comprises, in this example of an embodiment, four mold sections 32, 33 movable in relation to one another. In the four mold sections 32, 33, a mold cavity is defined which has four lobes in cross-section. The lobes are bounded each time on either side by ridges 34 protruding inwardly inside the mold cavity.

For the purpose of forming the balloon 30, a piece of tube-like basic material is placed inside the mold cavity and the mold sections 31, 32 are placed against each other, so that the mold cavity is defined. Next the material (of which a partial manufacture has been made) is heated and an overpressure is generated inside it, as a result of which this material will expand and place itself against the wall of the mold cavity. The balloon 30 will thus obtain the shape corresponding to that of the mold cavity. After cooling, the balloon member 30 can be taken from the mold.

According to the illustrated preferred embodiment, the partial manufacture has been formed with, in cross-section, alternating sections 35, 36 made of relatively stiff and pliable material respectively. The partial manufacture has been received in the mold 31 in such a way that the sections 35 containing relatively stiff material are positioned against the ridges 34. As a result, only the relatively pliable sections 36 expand during molding. The relatively stiff sections 35 form so to speak stiffening ribs in the material of the balloon 30. The lobes 37 are connected each time on both sides with such a stiffening rib.

Figure 6:
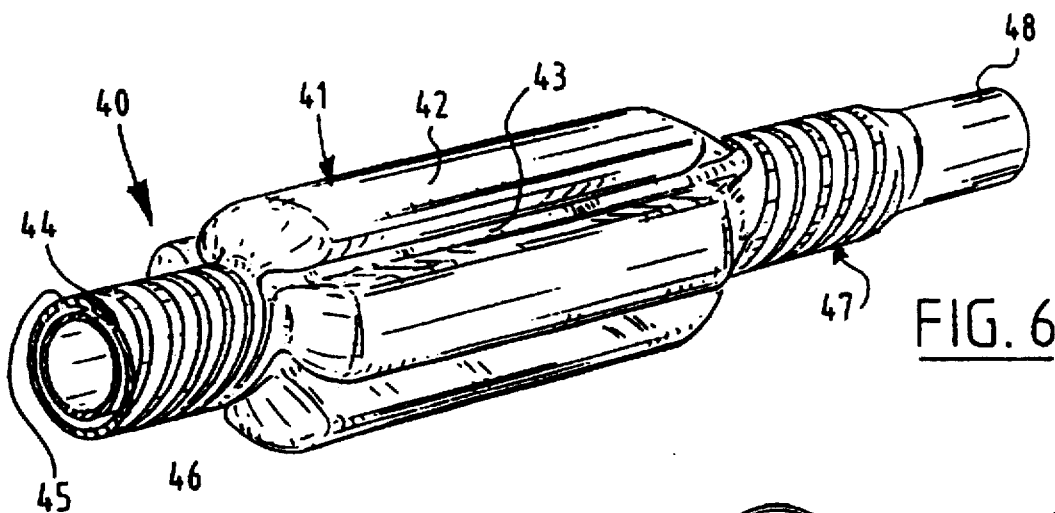
FIG. 6 is a partial view of another embodiment of the catheter according to the invention.

With the embodiment of the catheter 40 according to FIG. 6, which in partial manufacture the balloon 41 has been obtained by strip-shaped co-extrusion of relatively stiff material 44 and relatively pliable material 45. It is seen to that a good bond is obtained between the relatively stiff material and the relatively pliable material during co-extrusion. In a first section of the balloon 41, with which it is connected to the basic body, the strips 44, 45 have been extruded in a helical pattern by using a rotating extrusion head. In the expandable section of the balloon 41, the co-extruded bands of material 44, 45 extend axially as during the manufacturing process of the partial manufacture the rotating mold head has been stopped. Thus lobes 42 extending axially can be formed with bounded channels 43 inbetween. The end-section 47 first comprises a section in which the bands of material extend in a helical pattern and finally an end-section 48 comprising only the relatively pliable material 45. The supply of the relatively stiff material 44 has been switched off during the extrusion of this end-section 48.

Figure 7:
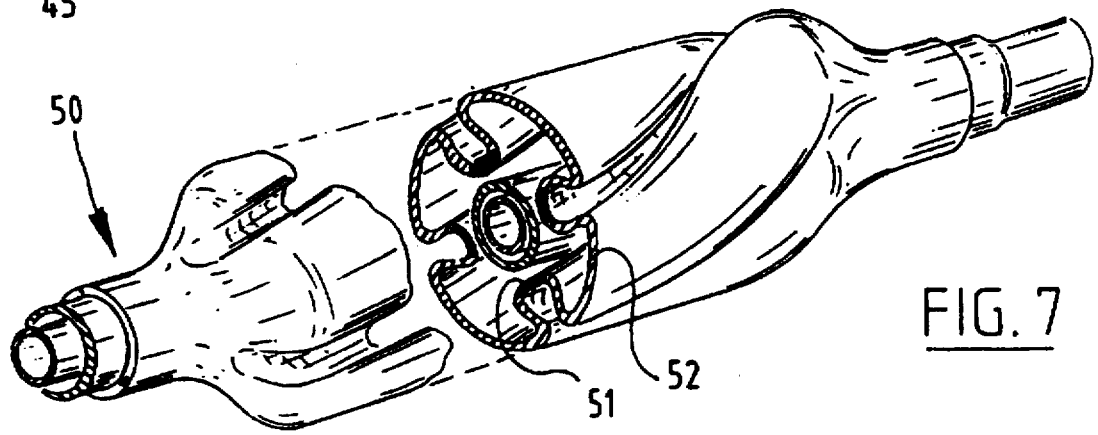
FIG. 7 is a partial view of yet another embodiment.

With the catheter 50 of FIG. 7, the relatively stiff sections 51 extend in a helical pattern with a large pitch. Consequently, the lobes 52 also extend in such a helical pattern. In the unexpanded state of this balloon, its lobes 52 can fold together into a small diameter, in particular by twisting the balloon member in the unexpanded state around its longitudinal axis. The lobes 52 are then folded closely against the basic body.

Also, it is to be realized that the relatively stiff sections of the balloon can be made of a thermoplastic material containing fibrous reinforcement or by using material which can be cross-linked. If the latter is the case, the balloon will be irradiated with, for instance, ultraviolet light or an electron beam. Consequently, transverse connections are formed between the molecules as a result of which the relatively stiff sections of the balloon are formed. These types of material have a high tensile strength following irradiation and provide a high degree of resistance against deformation when the balloon is being inflated.

The term "material" used in this application concerns both homogenous materials and non-homogenous materials. The non-homogenous materials include, for instance, materials containing fibrous or metal mesh reinforcement or materials to which additives have been added which form transverse connections or cross-links between the molecules as a result of irradiation with, for instance, ultraviolet light or an electron beam in order to provide this material with a greater stiffness and tensile strength.

We claim:

1. Catheter comprising:
    a tube-like basic body having a center with a proximal and a distal end;
    an expandable balloon member arranged close to the distal end of the basic body comprising a number of relatively stiff sections extending in a longitudinal direction of the basic body with relatively pliable sections extending between said stiff sections;
    wherein the balloon member is pre-formed such that in an expanded form the relatively stiff sections remain substantially at the same diameter from the center of the catheter as in a non-expanded form and the relatively pliable sections form lobes about said relatively stiff sections.

2. Catheter as claimed in claim 1, wherein the relatively stiff sections are formed by materials with a greater stiffness than the material of the relatively pliable sections.

3. Catheter as claimed in claim 2, wherein the relatively stiff sections are formed by material containing additives which have formed cross connections in the material at molecular level by irradiation with, for instance, ultraviolet light or an electron beam.

4. Catheter as claimed in claim 1, wherein the relatively stiff sections extend in a helical pattern.

5. Method for manufacturing a catheter comprising:

the providing of a piece of tube-like basic material with a center, the manufacturing of a balloon member by blow molding inside a mold and the arranging of the balloon member to the basic body, wherein the manufacturing of the balloon member comprises the providing of a mold with a mold cavity of which the cross-section is formed with lobes, the receiving inside the mold of a tube-like partial manufacture of the balloon being formed with, in cross-section, alternating sections of relatively stiff and relatively pliable material; positioning the partial manufacture with the sections of relatively stiff material against inwardly protruding ridges of the lobed mold cavity; and the deformation of the partial manufacture by blow molding until it corresponds to the shape of the mold cavity.

6. Method as claimed in claim 5, wherein the partial manufacture is manufactured by strip-like co-extrusion of relatively stiff and relatively pliable material.

7. Method as claimed in claim 6, wherein the partial manufacture is rotated in relation to an extrusion head during extrusion, so that the bands of material which are formed extend in a helical pattern.

* * * * *